United States Patent [19]

Beeby

[11] 3,983,113

[45] Sept. 28, 1976

[54] CEPHALOSPORIN TYPE ANTIBACTERIALS

[75] Inventor: Philip J. Beeby, Mountain View, Calif.

[73] Assignee: Syntex (U.S.A.) Inc., Palo Alto, Calif.

[22] Filed: Oct. 14, 1975

[21] Appl. No.: 621,717

Related U.S. Application Data

[63] Continuation-in-part of Ser. No. 605,109, Aug. 15, 1975.

[52] U.S. Cl. .................. 260/240 R; 260/243 C; 260/240.1; 424/246
[51] Int. Cl.² ................................ C07D 501/14
[58] Field of Search ......... 260/240 R, 240.1, 243 C; 424/246

[56] References Cited
UNITED STATES PATENTS

| | | |
|---|---|---|
| 3,660,395 | 5/1972 | Wright ........................... 260/243 C |
| 3,769,277 | 10/1973 | Long et al. ..................... 260/243 C |
| 3,830,700 | 8/1974 | O'Callaghan et al. ............. 424/246 |
| 3,852,277 | 12/1974 | Jacobus et al. ................... 424/246 |
| 3,929,780 | 12/1975 | Weir ............................... 260/243 C |

Primary Examiner—Arthur P. Demers
Attorney, Agent, or Firm—Natalie Jensen; William B. Walker

[57] ABSTRACT

3-[3-(1-Methyltetrazol-5-ylthio)-prop-1-(t)-enyl]-7β-(α-substituted acetamido)-ceph-3-em-4-carboxylic acid; 7β-(α-substituted acetamido)-3-[3-(1,2,4-triazol-5-ylthio)-prop-1-(t)-enyl]-ceph-3-em-4-carboxylic acid derivatives and salts thereof; and ester intermediates and processes for preparing such compounds. The compounds are useful as antibacterials and are active against a wide variety of gram positive and gram negative bacteria.

52 Claims, No Drawings

CEPHALOSPORIN TYPE ANTIBACTERIALS

CROSS REFERENCE TO RELATED APPLICATION

This application is a continuation-in-part of application U.S. Ser. No. 605,109, filed Aug. 15, 1975.

BACKGROUND OF THE INVENTION

1. The Invention

This invention relates to cephalosporin type compounds, having antibiotic activity, and intermediates and processes for preparing such compounds. In a further aspect, this invention relates to 3-[3-(1-methyltetrazol-5-ylthio)-prop-1-(t)-enyl]-7β-(α-substituted acetamido)-ceph-3-em-4-carboxylic acid; 7β-(α-substituted acetamido)-3-[3-(1,2,4-triazol-5-ylthio)-prop-1-(t)-enyl]-ceph-3-em-4-carboxylic acid; and to esters and salts thereof; and to methods for preparing such compounds. In a still further aspect, the invention relates to pharmaceutical compositions and antiseptic compositions containing such compounds and to methods of destroying and/or inhibiting the growth of gram negative and/or gram positive bacteria.

2. The Prior Art

Since the first discovery that certain derivatives of Cephalosporin C exhibit potent antibiotic activity, a large number of cephalosporin type compounds have been synthetized for possible improved, or different, antibiotic activity and selectivity note, for example, U.S. Pat. Nos. 3,769,277, 3,830,700, 3,853,860, 3,859,274, 3,864,338, 3,867,380 and 3,880,851. A general discussion of cephalosporins can be found in *Cephalosporins and Penicillins Chemistry and Biology*, edit E. H. Flynn, Academic Press, Inc. (1972).

SUMMARY

In summary, the compounds of the invention can be represented by the following generic formulas:

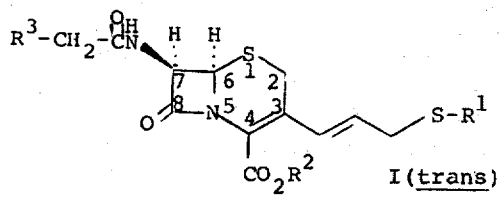

I(trans)

wherein $R^1$ is 1-methyltetrazol-5-yl; or 1,2,4-triazol-5-yl;

$R^2$ is hydrogen, or a protecting group selected from the group of diphenylmethyl, benzyl, o-nitrobenzyl, p-nitrobenzyl, 3,5-dinitrobenzyl, p-methoxybenzyl, t-butyl pivaloyloxymethyl, phenacyl, and polyhaloalkyl having two to six carbon atoms, e.g. 2,2,2-trichloroethyl;

$R^3$ is thiophen-2-yl; trifluoromethylthio, phenoxy, phenylthio, (1H)-tetrazol-1-yl, or sydnon-3-yl.

The pharmaceutically acceptable salts of the above compounds are also encompassed within the scope of the invention. Also, as can be seen from formula I, the stereo configuration of the propenyl double bond is trans and the

substituent at the 7-position is beta oriented.

In summary, one process of the invention comprises rearrangement of the C-2(3) double bond of the corresponding 3-[3-(heterocycle-ylthio)prop-1-(t)-enyl]-7β-(thiophen-2-yl-acetamido)-ceph-2-em-4-carboxylate intermediate to C-3(4) to yield the corresponding ester of formula I and optionally cleaving the carboxylate ester protecting group to yield the corresponding 4-carboxylic acid of formula I and optionally treating the acid with a pharmaceutically acceptable cation to yield the corresponding salt.

A further process of the invention comprises acylating the 7β-amino group of the corresponding cephem 4-carboxylic acid or 4-carboxylic ester and optionally hydrolyzing the 4-carboxylic ester protecting group to yield the corresponding 4-carboxylic acid of formula I, and, if desired, treating the acid with a pharaceutically acceptable cation to yield the corresponding salt.

In summary, the pharmaceutical compositions and antiseptic composition, of the invention, comprise the 4-carboxylic acid compounds of formula I, and/or pharmaceutically acceptable salt thereof, and a pharmaceutically acceptable carrier or antiseptic carrier.

In summary, the process of the invention for reducing or inhibiting bacterial infections comprises administering an effective amount of the carboxylic acids of formula I, or a pharmaceutically acceptable salt thereof, to mammals suffering from such infections, or in the case of undesired bacterial growth on inanimate objects, applying an effective amount of the aforementioned in compounds in an antiseptic carrier to such objects.

The invention will be further described hereinbelow.

FURTHER DESCRIPTION OF THE INVENTION AND PREFERRED EMBODIMENTS

The compounds of the invention can be represented by the following sub-generic formulas:

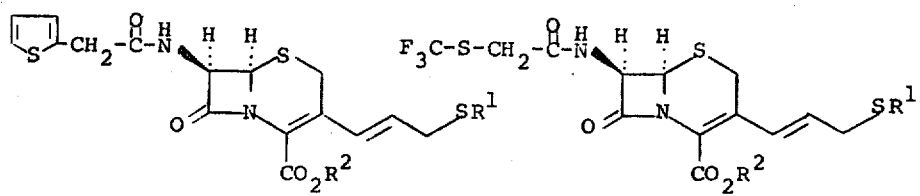

II  III

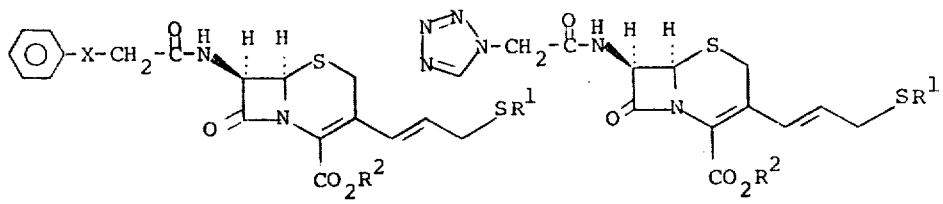

IV          V

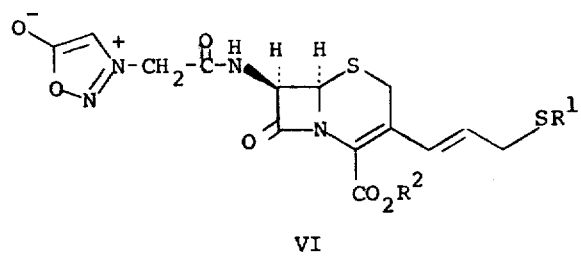

VI wherein
R[1] is 1-methyltetrazol-5-yl or 1,2,4-triazol-5-yl,
R[2] is hydrogen or a protecting group selected from the group of diphenylmethyl, benzyl, o-nitrobenzyl, p-nitrobenzyl, 3,5-dinitrobenzyl, p-methoxybenzyl, t-butyl, pivaloyloxymethyl, phenacyl, and polyhaloalkyl having two to six carbon atoms, e.g. 2,2,2-trichloroethyl;
X is oxo or thio.

Also encompassed within the invention are the pharmaceutically acceptable salts of the above compounds.

Also, as previously noted, the C-7 position amino or carbonylamino substituent is beta oriented and the propenyl double bond is trans oriented.

Typical illustrations of the compounds of formula II can be had by reference to Examples 3, 3A, 3B and 4A as set forth hereinbelow.

Typical illustrations of the compounds of formulas III, IV, V an VI can be had by reference to Examples 11, 12; 7, 8, 9, 10; 5, 6; and 13, 14, respectively, hereinbelow.

In terms of antibiotic activity, the preferred compounds of formula I, with respect to the R[1] substituent, are those wherein R[1] is 1-methyltetrazol-5-yl, the preferred R[3] substituents are (1H)-tetrazol-1-yl; trifluoromethylthio; and sydnon-3-yl. The particularly preferred compounds of formula I are:

7β-(α-(1H)-tetrazol-1-ylacetamido)-3-[3-(1-methyltetrazol-5-ylthio)-prop-1-(t)-enyl]-ceph-3-em-4-carboxylic acid;

7β-(α-trifluoromethylacetamido)-3-[3-(1-methyltetrazol-5-ylthio)-prop-1-(t)-enyl]-ceph-3-em-4-carboxylic acid;

7β-(α-sydnon-3-ylacetamido)-3-[3-(1-methyltetrazol-5-ylthio)-prop-1-(t)-enyl]-ceph-3-em-4-carboxylic acid; and pharmaceutically acceptable salts thereof.

In terms of convenience, the sodium salts are preferred, correspondingly the particularly preferred salts are the sodium salts of the preferred and particularly preferred compounds of formula I.

The processes for preparing the compounds of the invention can be schematically represented by the following sequence of overall reaction equations:

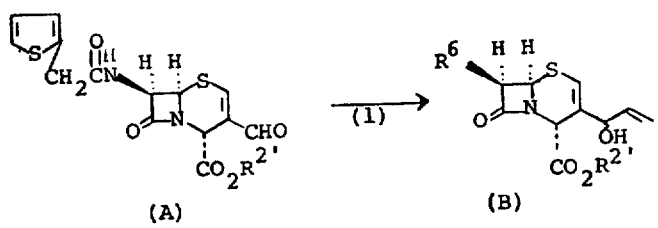

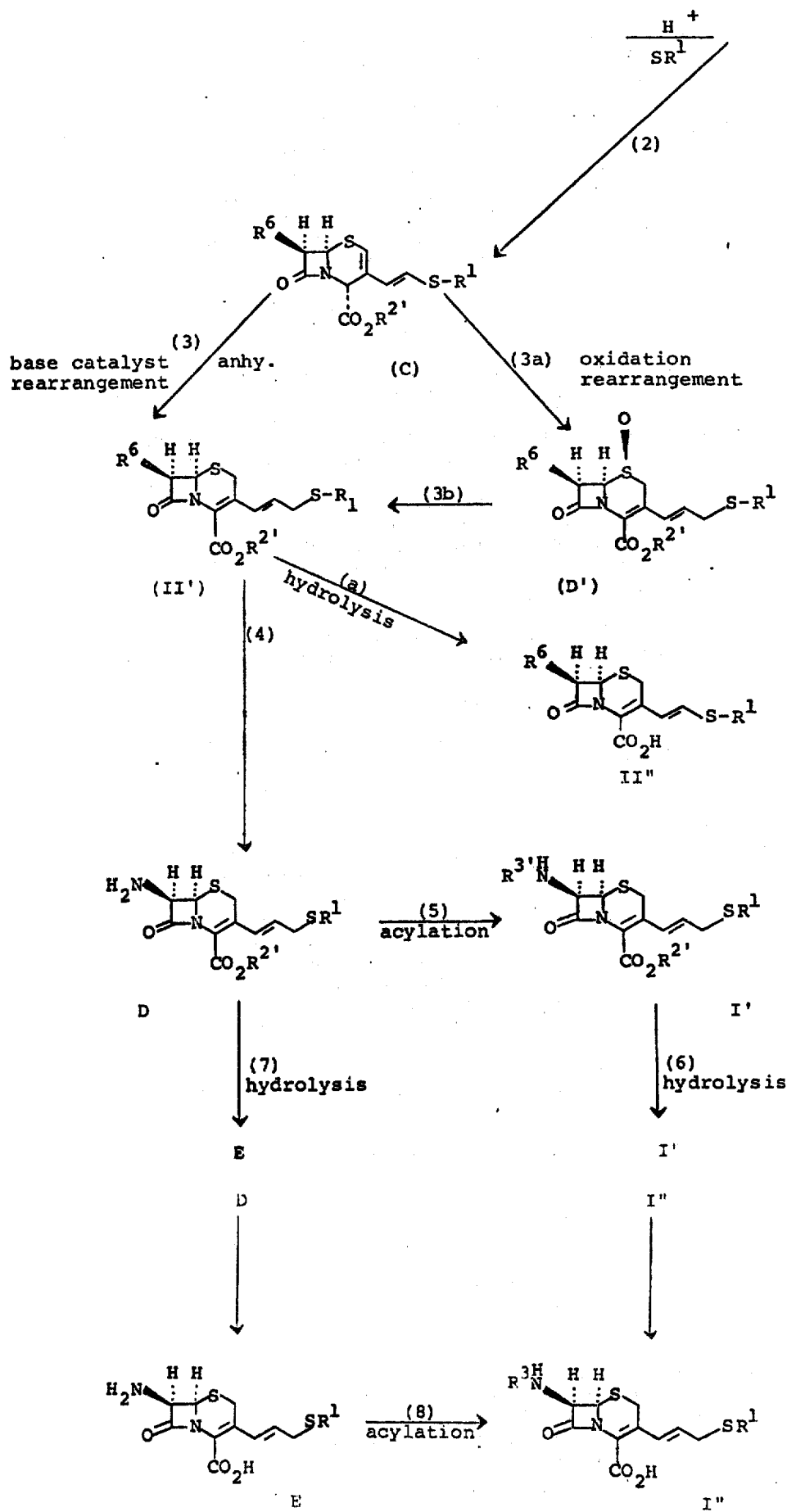

wherein
R²' is a suitable protecting group, e.g. diphenylmethyl,
R¹ and R³ are as defined hereinabove, and
R⁶ is the group:

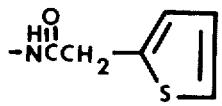

Step 1, of the above process, can be conveniently effected by treating the starting material of formula A with a suitable vinyl Grignard reagent, preferably in a suitable inert organic solvent. Typically, this treatment is conducted at temperatures in the range of −100° to −20°C, preferably about from −60° to −80°C, for about from 0.25 to 2.0 hours, and preferably about from 0.25 to 0.5 hours. Typically, a mole ratio of Grignard reagent to compound of formula A of about from 3 to 10, preferably about from 4 to 5, is used. Typically, and preferably, the treatment is conducted under anhydrous conditions and under an inert atmosphere; e.g. nitrogen. Suitable inert organic solvents which can be used include, for example, tetrahydrofuran, dimethoxyethane, dioxane and the like, and mixtures thereof. Suitable Grignard reagents which can be used include, for example, vinyl magnesium chloride, vinyl magnesium bromide and the like. The resulting product is a mixture of α- and β-hydroxy isomers which, if desired, can be resolved by conventional procedures.

The starting materials of formula A are known compounds and can be prepared according to known procedures such as, for example, described in U.S. Pat. No. 3,864,338, and in the Preparations set forth hereinbelow; or by obvious modifications of such procedures; e.g. by substitution of protecting groups.

Step 2, of the process, can be conveniently effected by treating the compound of formula B (either the respective α- or β-hydroxy isomers or mixtures thereof) with a mercapto substituted heterocycle corresponding to the desired SR¹ substituent, in the presence of a small amount of a strong acid (e.g. typically about 0.01 to 0.1 moles per mole of the compound of formula B). Typically, this treatment is conducted at temperatures in the range of about from 0° to 50°C, preferably about from 35° to 45°C for about from two to 24 hours, preferably about from six to eight hours using mole ratios of mercapto heterocycle to the compound of formula B of about from 1.0 to 5.0., preferably about from 1.1 to 1.5. Suitable inert inorganic solvents which can be used include, for example, tetrahydrofuran, dimethoxyethane, dioxane, chloroform, methylene chloride and the like. Suitable inert strong acids which can be used include, for example, perchloric acid, hydrochloric acid, hydrobromic acid, sulfuric acid, and the like. Suitable oganic acids which can be used include, for example, p-toluenesulfonic acid, trifluoroacetic acid, and the like. Typically, superior results are obtained using p-toluenesulfonic acid.

Step 3, rearrangement of the cephem double bond and the orientation of the C-4-position ester group, can be conveniently effected by treating the compound of formula C with a catalytic amount of triethylamine in pyridine. Typically, this treatment is conducted under anhydrous conditions at temperatures in the range of about from 0° to 40°C, preferably about from 20° to 25°C for about from 10 to 72 hours, preferably about from 24 to 36 hours using mole ratios of triethylamine to compound of formula C of about from 0.01 to 1.0, and preferably about from 0.05 to 0.1. Suitable organic solvents which can be used include, for example, pyridine, quinoline, N,N-dimethylaniline, and the like, and mixtures thereof. Also, in place of triethylamine, the following reagents could also be used, diisopropylethylamine, 1,6-diazabicyclo[5,4,0]undec-non-1-ene, 1,5-diazabicyclo [4,3,0]non-1-ene and the like. Alternatively, this rearrangement can be effected in two steps (3a and 3b) via the intermediate D'. Step 3a can be conveniently effected by treating the compound of formula C with m-chloroperbenzoic acid in a suitable inert organic solvent. Typically, this treatment is conducted at temperatures in the range of about from −10° to 25°C, preferably about from 0° to 5°C for about from 0.5 to 24 hours, preferably about from three to five hours, using mole ratios of m-chloroperbenzoic acid to compound of formula C of about from 1.0 to 1.2. Preferably this mole ratio should be close to one (about from 1.05 to 1.1) to prevent over oxidation of the thio moiety to sulfonyl). Suitable inert organic solvents which can be used include, for example, methylene chloride, chloroform, and the like, and mixtures thereof. Also, in place of m-chloroperbenzoic acid, the following reagents could also be used, perbenzoic acid, peracetic acid, hydrogen peroxide, sodium metaperiodate, ozone, and the like. Step 3b can be conveniently effected by treating the sulfo oxide of formula D' with a mixture of stannous chloride and acetyl chloride in a suitable inert organic solvent, preferably under an inert atmosphere. Typically, this treatment is conducted at temperatures in the range of about from −10° to 25°C, preferably from 0° to 5°C for about from 0.25 to 5.0 hours, preferably about from 1.0 to 2.0 hours using mole ratios of stannous chloride to compound of formula D' of about from 1.5 to 5.0, and preferably about from 2.0 to 3.0. Also, in place of stannous chloride and acetyl chloride, the following reagents could also be used, phosphorous trichloride, phosphorous tribromide and the like, and mixtures thereof.

Step 4 of the process can be conveniently effected by treating the compound of formula II' with phosphorous pentachloride in an inert organic solvent, in the presence of pyridine. This portion of step 4 is typically conducted under anhydrous conditions and under an inert atmosphere at temperatures in the range of about from 10° to 30°C for about from 2.0 to 4.0 hours using 1.1 to 1.2 moles of pyridine and about from 1.1 to 1.2 moles of phosphorous pentachloride per mole of compound of formula II'. After the resulting reaction has been substantially completed, about from two to 10 moles of isobutyl alcohol, preferably about five, per mole of formula II' is added to the product mixture, and the treatment continued at temperatures in the range of about from −20° to 30°C, preferably about from 0° to 5°C for about from 0.25 to 2.0 hours, preferably about from 0.5 to 1.0 hours. A small quantity of water is then added to effect the final reaction in this treatment. This final step is typically conducted at temperatures in the range of −20° to 30°C, preferably about from 0° to 5°C for about from 0.1 to 1.0 hours, preferably about from 0.25 to 0.5 hours. Suitable inert organic solvents which can be used for this treatment include, for example, chloroform, and the like. Also, in place of pyridine, the following compounds could, for example, be used, quinoline, N,N-dimethylaniline, and the like. Also, in place of isobutyl alcohol, other lower alkanols could be used, for example, methanol, ethanol, and the like or mixtures thereof.

The next two steps of the process, i.e. acylation of the amino group and, if desired, removal of the ester group can be conducted interchangeably. Hence, the ester group can first be cleaved (step 7) and then the amino group acylated (step 8), or vice versa (i.e. steps 5 and 6). Step 7 or 6, and step 4a, can be effected by conventional procedures used by the art to cleave ester groups to yield the corresponding free acid, for example, benzhydryl and p-methoxybenzyl can be conveniently cleaved via treatment with a trifluoroacetic acid-anisole mixture (typically 2:1 to 6:1 mole ratio) at 0°–5°C for about from two to five minutes in an inert solvent; e.g. methylene chloride, benzene, and the like.

Steps 5 and 8 can be effected by conventional amino acylation procedures. For example, steps 5 and 8 can be conveniently effected by treating the compound of formulas D and E with about from 1.1 to 1.5 stoichiometric equivalents of an acyl halide, having the desired $R^3$-methylenecarbonyl acyl moiety, in an inert organic solvent (e.g. dichloromethane, chloroform, etc.) in the presence of an organic or inorganic base (e.g. sodium bicarbonate; pyridine; triethylamine and the like) at temperatures in the range of about from 0° to 5°C for about from 0.5 to one hour. Typically, about from two to 10 stoichiometric equivalents of the base is used. The acylation can also be effected via treatment with a carboxy acid, having the desired $R^3$ moiety (i.e. $R^3COOH$) and a suitable coupling reagent, e.g. dicyclohexyl carbodiimide, N-ethoxycarbonyl-2-ethoxy-1,2-dihydroquinoline, in a suitable inert organic solvent, e.g. dichloromethane.

It is generally preferred that the respective products of each process step, described hereinabove, be separated and/or isolated prior to its use as starting material for subsequent steps. Separation and isolation can be effected by any suitable or purification procedure such as, for example, evaporation, crystallization, column chromatography, thinlayer chromatography, distillation, etc. Specific illustrations of typical separation and isolation procedures can be had by reference to the appropriate examples described hereinbelow; however other equivalent separation procedures could, of course, also be used. Also, it should be appreciated that where typical reaction conditions (e.g. temperatures, mole ratios, reaction times) have been given that conditions both above and below these ranges can also be used, though generally less conveniently.

The pharmaceutically acceptable salts, of the invention, can be prepared according to procedures which are well known in the art, for example, by simply treating the free acid of formula I with an inorganic or organic base having the desired salt cation, e.g. sodium hydroxide, potassium hydroxide, triethylamine, ethanolamine, tris(hydroxymethyl)aminomethane, etc. The sodium salts can also be conveniently prepared by treating a solution of the acid in ethyl acetate with an excess of sodium-2-ethyl hexanoate.

The acids and salts, of the invention, have a broad spectrum of antibacterial activity against both gram positive and gram negative organisms such as *Staphylococcus aureus*, *Proteus vulgaris*, *Escherichia coli*, *Streptococcus pyogenes*, *Klebsiella pneumoniae*, and *Shigella sonnei*. The compounds can be used to combat or prophylactically to prevent infections of this nature in mammals and can be administered in the same manner as cephalothin or cephalosporin derivative drugs are generally administered (typically parenterally or orally). The compounds can be administered in a wide variety of dosage forms, either alone or in combination with other pharmaceutically compatible medicaments, in the form of pharmaceutical compositions suited for oral or parenteral administration. The dosage forms typically comprise the compounds (typically as pharmaceutically acceptable salts) and a pharmaceutically carrier and are preferably formulated in unit dosage form to facilitate the simple administration of precise dosages. The pharmaceutical carrier can be either a solid material or liquid, in which the compound is dissolved, dispersed or suspended. The dosage form can optionally contain other compatible medicaments, preservatives, emulsifying agents, wetting agents and/or pH-buffering agents. Suitable preservatives which can be used include, for example, benzyl alcohol and the like. Suitable buffering agents include, for example, sodium acetate and pharmaceutical phosphate salts and the like. Liquid dosage forms include, for example, solutions, suspensions, emulsions, syrups, elixirs, etc. Liquid carriers include, for example, water, saline solution, etc. Solid dosage forms include, for example, tablets, powders, capsules, pills, etc. Suitable solid carriers include, for example, pharmaceutical grades of starch, lactose, sodium saccharin, sodium bisulfite and the like.

The compounds of this invention are typically administered in dosages of about from 10 to 100 mg. per kg. per day of body weight. The precise effective dosage will, of course, vary depending upon the mode of administration, the condition being treated and the host.

The compounds can also be used as antiseptic agents in cleaning or disinfecting compositions, typically in solution form or suspended in a liquid carrier or in an aerosol spray.

Definitions

The following terms, as used hereinabove and below, have the following meaning unless expressly stated to the contrary. The term lower alkyl refers to alkyls having from one through six carbon atoms and includes both straight chain and branched chain alkyls such as, for example, methyl, ethyl, isopropyl, t-butyl, pentyl, n-hexyl, isohexyl, and the like. The term lower alkoxy refers to alkoxy groups having from one through six carbon atoms and can be defined as the group -OR' wherein R' is lower alkyl as defined hereinabove. The term halo or halide refers to the group of fluoro, chloro, bromo, and iodo or the corresponding halides. The term pharmaceutically acceptable salts refers to those salts of the parent compound which do not significantly adversely affect the pharmaceutical properties (e.g. toxicity, effectiveness, etc.) of the parent compound such as, for example, are conventionally used in the pharmaceutical art. The salts of the present invention are pharmaceutically acceptable cation salts, with respect to the acid and sulfo moieties of the compounds of formulas III and IV, and in case of formula III wherein $R^4$ is carboxy or sulfo can be prepared as both mono and bis salts. Suitable pharmaceutically acceptable cations include, for example, the alkali metals, e.g. sodium, potassium, etc.; alkali earth metals, e.g. calcium, etc.; ammonia; organic salts of triethylamine, diethylamine, tris(hydroxymethyl)aminomethane, ethanolamine, choline, caffeine and the like. The term 1-methyltetrazol-5-yl refers to the radical having the formula

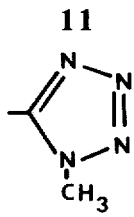

and the term 1,2,4-triazol-5-yl refers to the radical having the formula

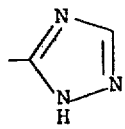

The term room temperature refers to about 20° Centigrade and all temperatures and temperature ranges refer to degrees centigrade. All percents refer to weight percents and the term equivalent mole amount refers to an amount stoichiometrically equivalent to the other reactant in the reaction referred to.

The term benzhydryl refers to the radical diphenylmethyl, i.e.

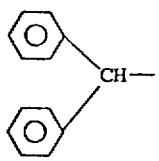

The term sydnon-3-yl refers to the radical having the formula

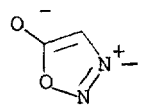

A further understanding of the invention can be had from the following non-limiting preparations and examples. Wherein proton magnetic resonance spectrum (n.m.r.) are determined at 100 mHz (the signs of the coupling constants are not assigned) and signals are assigned as singlets (s), broad singlet (bs), doublets (d), double doublets (dd), triplets (t), double triplets (dt), quartets (q) and multiplets (m).

PREPARATION 1

3-Acetoxymethyl-7β-(thiophen-2-yl-acetamido)-ceph-2-em-4-carboxylic acid

In this preparation 42 g. of cephalothin (i.e. 3-acetoxymethyl-7β-(thiophen-2-yl-acetamido)-ceph-3-em-4-carboxylic acid) is dissolved with warming in 130 ml. pyridine, and then cooled to about 18°C. 13 Ml. of acetic anhydride is added and the resulting mixture allowed to stand for two hours at room temperature affording a crystalline precipitate. Then 250 ml. of a 65:35, by vol., ethyl ether/ethyl acetate mixture is added and the resulting mixture stirred for one hour and then filtered. The recovered crystals are washed with 65 ml. of 65:35, by vol., ethyl acetate/ethyl ether solution and dried under vacuum to give 41 g. of the pyridinium salt of 3-acetoxymethyl-7β-(thiophen-2-yl-acetamido)-ceph-2-em-4-carboxylic acid. This salt is added to a mixture of 650 ml. water and 650 ml. ethyl acetate and the mixture then acidified to pH 2 using 20% aqueous hydrochloric acid. The ethyl acetate layer is separated and the aqueous layer further extracted with 400 ml. ethyl acetate. The combined ethyl acetate extracts are washed twice with brine, dried over anhydrous sodium sulfate and the solvent then removed under reduced pressure to afford 34 g. of 3-acetoxymethyl-7β-(thiophen-2-yl-acetamido)-ceph-3-em-4-carboxylic acid.

PREPARATION 2

3-Hydroxymethyl-7β-(thiophen-2-yl-acetamido)-ceph-2-em-4-carboxylic acid

In this preparation 34 g. of 3-acetoxymethyl-7β-(thiophen-2-yl-acetamido)-ceph-2-em-4-carboxylic acid is added to a solution of 8.4 g. of lithium hydroxide monohydrate in 1000 ml. of water. The mixture is stirred at room temperature under nitrogen for two hours and then layered with 600 ml. of ethyl acetate. The pH of the mixture is then readjusted to pH 2 by the addition of 20% aqueous hydrochloric acid (~50 ml.). The ethyl acetate layer is separated and the aqueous layer is extracted twice with 500 ml. portions of ethyl acetate. The combined ethyl acetate extracts are washed twice with brine, dried over anhydrous sodium sulfate and evaporated to dryness under reduced pressure affording 24.2 g. of 3-hydroxymethyl-7β-(thiophen-2-yl-acetamido)-ceph-2-em-4-carboxylic acid.

PREPARATION 3

Benzhydryl 3-hydroxymethyl-7β-(thiophen-2-yl-acetamido)-ceph-2-em-4-carboxylate

In this preparation 24.2 g. of 3-hydroxymethyl-7β-(thiophen-2-yl-acetamido)-ceph-2-em-4-carboxylic acid is dissolved in 800 ml. of tetrahydrofuran, and then with 15 g. of diphenyldiazomethane is added and the resulting mixture stirred at room temperature for three hours. The mixture is evaporated to dryness under reduced pressure and 250 ml. of 90:10, vol., ethyl ether/methylene chloride solution is added to the residue. After the mixture is stirred for four hours, the solid is recovered by filtration, and washed with 100 ml. of 90:10 ethyl ether/methylene chloride and then dried affording 28.5 g. of benzhydryl 3-hydroxymethyl-7β-(thiophen-2-yl-acetamido)-ceph-2-em-4-carboxylate.

PREPARATION 4

Benzhydryl 3-formyl-7β-(thiophen-2-yl-acetamido)-ceph-2-em-4-carboxylate

In this preparation 31 g. of dried chromium trioxide is added to a mixture of 51 g. of dry pyridine and 800 ml. of dry methylene chloride and stirred at 15°C under nitrogen for 20 minutes. 26 Grams of benzhydryl 3-hydroxymethyl-7β-(thiophen-2-yl-acetamido)-ceph-2-em-4carboxylate in 250 ml. of dry methylene chloride is added in one portion. The resulting mixture is stirred for 30 minutes and then filtered through diatomaceous earth. The contents of the reaction flask and the diatomaceous earth are washed with 500 ml. of methylene chloride and combined with the preceding filtrate and then washed with 400 ml. of 5% aqueous potassium hydroxide solution, 500 ml. of 20% aqueous hydrochloric acid and twice with 400 ml. brine. The aqueous washings are back extracted with 500 ml. of methylene chloride and the extracts added to the previously washed methylene chloride filtrate, then dried over sodium sulfate and then stirred for one hour with 30 g.

of silica gel. The mixture is filtered and the silica gel washed with 400 ml. 1:1 vol. ethyl acetate/methylene chloride. The combined filtrates are evaporated to dryness under reduced pressure and the resulting residue (26 g.) is recrystallized from ethyl ether/methylene chloride affording 21.4 g. of benzhydryl 3-formyl-7β-(thiophen-2-yl-acetamido)-ceph-2-em-4-carboxylate.

EXAMPLE 1

This example illustrates step 1 of the process for preparing the compounds of the invention. In this example 2.5 g. of benzhydryl 3-formyl-7β-(thiophen-2-yl-acetamido)-ceph-2-em-4-carboxylate in 50 ml. of anhydrous tetrahydrofuran is stirred under nitrogen at −70°C and 10 ml. of 2.5 molar solution of vinyl magnesium chloride is added dropwise over five minutes. After 15 minutes, 50 ml. of pH 7 buffer solution of dibasic sodium phosphate and monobasic potassium phosphate is added to the well stirred mixture, and then warmed to room temperature. The mixture is diluted with 200 ml. of water and layered with 200 ml. of ethyl acetate. The pH of the aqueous layer is adjusted to pH 4 by the addition of 20% aqueous hydrochloric acid. The ethyl acetate layer is separated and the aqueous layer extracted with 100 ml. ethyl acetate. The ethyl acetate extracts are combined and then washed twice with 50 ml. portions of brine, dried over sodium sulfate and evaporated under reduced pressure affording benzhydryl 3-(1-hydroxy-prop-2-enyl)-7β-(thiophen-2-yl-acetamido)-ceph-2-em-4-carboxylate as a pale yellow oil (2.7 g.).

The two isomers (α-hydroxy and β-hydroxy) are separated using thick-layer of column chromatography on silica gel using 45:5 vol./vol. of methylene chloride-/acetone. They are then characterized by their nmr spectra (both oils).

Isomer 1 (higher Rf), nmr (CDCl₃) γ:3.78s,

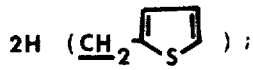

4.596bd, J 14Hz, 1H (HC-OH); 4.9-5.7m, 6H (H-6, H-7, H-4 + CH=CH₂); 6.366s, 1H (H-2); 6.7-7.5m,

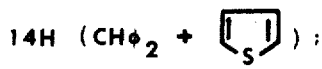

Isomer 2 (lower Rf), nmr (CDCl₃) γ:3.79s,

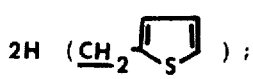

4.63m, 1H (HC—OH); 5.0-5.8m, 6H (H-6, H-7, H-4 + CH=CH₂); 6.25s, 1H (H-2); 6.8-7.5m,

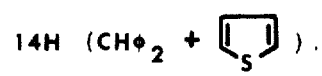

EXAMPLE 2

This example illustrates step 2 of the process for preparing the compounds of the invention. In this example, a 2.7 g. of the benzhydryl 3-(1-hydroxyprop-2-enyl)-7β-(thiophen-2-yl-acetamido)-ceph-2-em-4-carboxylate is dissolved in 30 ml. tetrahydrofuran and stirred at 40°C, and 5-mercapto-1-methyltetrazole (0.6 g.) and about 50 mg. of p-toluenesulfonic acid are added. The mixture is stirred for five hours at 40°C, then poured into 200 ml. of saturated aqueous sodium bicarbonate solution and extracted twice with 200 ml. portions of ethyl acetate. The ethyl acetate extracts are combined and washed with brine, dried over sodium sulfate and evaporated to dryness under reduced pressure affording 2.8 g. of a orange oil. This was chromatographed on 200 g. of silica gel eluting with 6:4 vol. ratio of ethyl acetate/hexane. The fractions which are homogeneous by thin-layer chromatography are combined affording 2.1 g. of the benzhydryl 3-[3-(1-methyltetrazol-5-ylthio)-prop-1-(t)-enyl]-7β-(thiophen-2-yl-acetamido)-ceph-2-em-4-carboxylate as a pale yellow glass, [α]$_D$ (CHCl₃) + 321°; uv (EtOH) 284 nm (ε21,600); ir (KBr) 1780, 1740, 1675 cm⁻¹; nmr (CDCl₃):3.80s, 3H (N—Me); 3.82s,

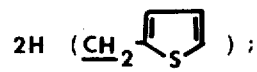

~3.8, 2H (CH₂—S, hidden by preceding signals); 5.2, 2H (H-6 + H-4); 5.56dd, J 4, 8Hz, 1H (H-7); 5.7dt, J 7, 16Hz, 1H (H-2'); 6.2d, J 16Hz, 1H (H-1'); 6.27s, 1H (H-2); 6.51d, J 8Hz, 1H (N-H); 6.8-7.4m,

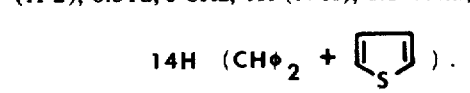

Similarly, benzhydryl 3-[3-(1,2,4-triazol-5-ylthio)-prop-1-(t)-enyl]-7β-(thiophen-1-yl-acetamido)-ceph-2-em-4-carboxylate (oil, nmr (CDCl₃):360d, J 7Hz, 2H (3'-CH₂), 3.82s,

5.16d, J 4.5Hz, 1H (H-6); 5.20s, 1H (H-4); 5.49dd, J 4.5, 8Hz, 1H (H-7); 5.69dt, J 16, 7 Hz, 1H (H-2'); 5.98d, J 16Hz, 1H (H-1'); 6.14s, 1H (H-2); 6.83s, 1H (CHφ₂); 6.9-7.4m,

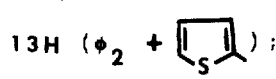

8.02s,

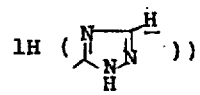

is prepared by following the same procedure but using 5mercapto-1,2,4-triazole in place of 5-mercapto-1-methyltetrazole.

EXAMPLE 3

This examples illustrates step 3 of the process of the invention for preparing the compounds of the invention. In this example, a solution of 0.9 g. of the benzhydryl 3-[3-(1-methyltetrazol-5-ylthio)-prop-1-(t)-enyl]-7β-(thiophen-2-yl-acetamido)-ceph-2-em-4-carboxylate in 5 ml. of dry pyridine is treated with 0.1 ml. of triethylamine. The mixture is allowed to stand at room temperature for 20 hours and then evaporated to dryness under reduced pressure. The resulting residue is chromatographed on 100 g. of silica gel eluting with 15% vol. ethyl acetate/benzene affording 300 mg. of benzhydryl 3-[3-(1-methyltetrazol-5-ylthio)-prop-1-(t)-enyl]-7β-(thiophen-2-yl-acetamido)-ceph-3-em-4-carboxylate and 500 mg. of the starting material of benzhydryl 3-[3(1-methyltetrazol-5-ylthio)-prop-1-(t)- enyl]-7β-(thiophen-2-yl-acetamido)-ceph-2-em-4-carboxylate. The recovered starting material is treated in the same manner as above, affording another 150 mg. of benzhydryl 3-[3-(1-methyltetrazol-5-ylthio)-prop-1-(t)-enyl]-7β-(thiophen-2-yl-acetamido)-ceph-3-em-4-carboxylate and 250 mg. of recovered benzhydryl 3-[3-(1-methyltetrazol-5-ylthio)-prop-1-(t)-enyl]-7β-(thiophen-2-yl-acetamido)-ceph-2-em-4-carboxylate; white solid, m.p. 90°–95° (dec.); [α]$_D$ –158° (CHCl$_3$); uv (EtOH):301 nm (ε 19,400); ir (KBr):1785, 1720, 1680cm$^{-1}$; nmr (CDCl$_3$):3.4m, 2H (2-CH$_2$); 3.80s,

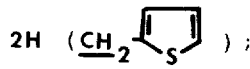

3.83s, 3H (N—Me); 3.91d, J 7.5Hz, 2H (3'-CH$_2$); 4.95d, J 4.5Hz, 1H (H-6); 5.79dd, J 4.5, 9 Hz, 1H (H-7); 6.08dt, J 16, 7.5Hz, 1H (H-2'); 6.63d, J 9Hz, 1H (N—H); 6.8-7.5m,

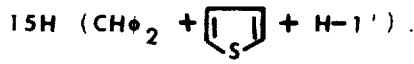

Anal. Found: C, 58.06; H, 4.65; N, 12.58. C$_{31}$H$_{28}$N$_6$O$_4$S$_3$ requires C, 57.75; H, 4.38; N, 13.03.

Similarly, benzhydryl 3-[3-(1,2,4-triazol-5-ylthio)-prop-1-(t)-enyl]-7β-(thiophen-2-yl-acetamido)-ceph-3-em-4-carboxylte (m.p. 183°–185°; [α]$_D$ –87° (dioxane); uv (EtOH) 306 nm (ε19,100); ir (KBr) 1790, 1705, 1665cm$^{-1}$; nmr (DMSO-d$_6$); 3.33bs, 2H (2-CH$_2$); 3.69d, J 7Hz, 2H (3'-CH$_2$); 3.79s,

5.20d, J 4.5Hz, 1H (H-6); 5.75dd, J 4.5, 8 Hz, 1H (H-7); 6.22dt, J 16, 7 Hz, 1H (H-2'); 6.69d, J 16Hz, 1H (H-1'); 6.9–7.6m,

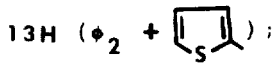

8.39s,

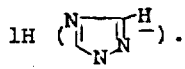

Analysis Found: C, 58.93; H, 4.55; N, 10.96. C$_{31}$H$_{27}$N$_5$O$_4$S$_3$ requires C, 59.12; H, 4.32; N, 11.12%) is prepared by following the same procedure but using benzhydryl 3-[3-(1,2,4-triazol-5-ylthio)-prop-1-(t)-enyl]-7β-(thiophen-2-yl-acetamido)-ceph-2-em-4-carboxylate in place of benzhydryl 3-[3-(1-methyltetrazol-5-ylthio)-prop-1-(t)-enyl]-7β-(thiophen-2-yl-acetamido)-ceph-2-em-4-carboxylate.

EXAMPLE 3A

This example illustrates step 3a of the process of the invention for preparing the compounds of the invention. In this example, 1.0 g. of benzhydryl 3-[3-(1-methyltetrazol-5-ylthio)-prop-1-(t)-enyl]-7β-(thiophen-2-yl-acetamido)-ceph-2-em-4-carboxylate in 25 ml. of methylene chloride was stirred at 0°C and m-chloroperbenzoic acid (0.3 g.) is added in portions over two hours. The mixture is further diluted with methylene chloride and washed with excess dilute aqueous sodium bicarbonate solution, dried over anhydrous sodium sulfate and evaporated under reduced pressure to give a yellow foam. This is chromatographed on silica gel, eluting with acetone/methylene chloride 15:85 vol. The pure fractions are combined affording 0.6 g. of the benzhydryl 3-[3-(1-methyltetrazol-5-ylthio)-prop-1-(t)-enyl]-7β-(thiophen-2-yl-acetamido)-ceph-3-em-4-carboxylate-1-oxide as a white crystalline solid, m.p. 125°–127°C; [α]$_D$ –204° (CHCl$_3$); uv (EtOH) 307 nm (ε 20,200); ir (KBr) 1790, 1720, 1680 cm$^{-1}$; nmr (CDCl$_3$) 3.06d, 3.95d, J 19Hz, 2H (H-2α and H-2β); 3,82s,

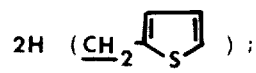

3.85s, 3H (N-Me); 3.92d, J 7 Hz (3'-CH$_2$); 4.47d, J 4.5 Hz (H-6); 5.9–6.3m, 2H (H-7 and H-2'); 6.8-7.6m,

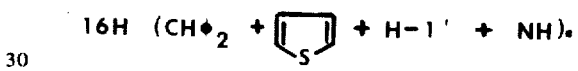

Anal. Found: C, 56.16; H, 4.18; N, 12.49. C$_{31}$H$_{28}$N$_6$O$_5$S$_3$ requires C, 56.35; H, 4.27; N, 12.72.

Similarly, benzhydryl 3-[3-(1,2,4-triazol-5-ylthio)-prop-1-(t)-enyl]-7β-(thiophen-2-yl-acetamido)-ceph-3-em-4-carboxylate-1-oxide is prepared by following the same procedure but using benzhydryl 3-[3-(1,2,4-triazol-5-ylthio)-prop-1-(t)-enyl]-7β-(thiophen-2-yl-acetamido)-ceph-2-em-4-carboxylate as the starting material.

EXAMPLE 3B

This example illustrates step 3b of the process of the invention for preparing the compounds of the invention. In this example, 0.5 g. of the benzhydryl 3-[3-(1-methyltetrazol-5-ylthio)-prop-1-(t)-enyl]-7β-(thiophen-2-yl-acetamido)-ceph-3-em-4-carboxylate-1-oxide is dissolved in 10 ml. of dry dimethylformamide and the solution stirred at 0°C under nitrogen while stannous chloride (0.5 g.) and acetyl chloride (1 ml.) are added and is stirred at 0°C for 15 minutes. Stirring is continued while the solution is warmed to room temperature and continued for another 20 minutes. The mixture is then diluted with water and extracted twice with ethyl acetate. The combined extracts are washed twice with water and brine, dried over sodium sulfate and evaporated under reduced pressure affording 0.6 g. of a yellow oil. This is chromatographed on silica gel eluting with acetone/methylene chloride (5:95 vol.) yielding 0.40 g. of the benzhydryl 3-[3-(1-methyltetrazol-5-ylthio)-prop-1-(t)-enyl]-7β-(thiophen-2-yl-acetamido)-ceph-3-em-4-carboxylate as a white crystalline solid Similarly, benzhydryl 3-[3-(1,2,4-triazol-5-ylthio)-prop1-(t)-enyl]-7β-(thiophen-2-yl-acetamido)-ceph-3-em-4-carboxylate is prepared by following the same procedure but using benzhydryl 3-[3-(1,2,4-triazol-5- ylthio)-prop-1-(t)-enyl]-7β-(thiophen-2-yl-acetamido)-ceph-3-em-4-carboxylate-1-oxide as the starting material.

EXAMPLE 4

This example illustrates step 4 of the process of the invention for preparing the compounds of the invention. In this example, 0.25 g. of the benzhydryl 3-[3-(1-methyltetrazol-5-ylthio)-prop-1-(t)-enyl]-7β-(thiophen-2-yl-acetamido)ceph-3-em-4-carboxylate is stirred at room temperature under nitrogen in 6 ml. of dry methylene chloride and 60 μl. of pyridine and 100 mg. of phosphorous pentachloride are added. The mixture is stirred for two hours at room temperature, then cooled to 0°C and 0.1 ml. of isobutyl alcohol is added and stirring continued for 40 minutes. Then 0.5 ml. of water is added and the mixture was stirred vigorously for 15 minutes. The mixture is then diluted with excess dilute aqueous sodium bicarbonate solution and extracted twice with ethyl acetate. The combined extracts are washed with water and brine, dried over sodium sulfate, and evaporated under reduced pressure affording the crude benzhydryl 3-[3-(1-methyltetrazol-5-ylthio)-prop-1-(t)-enyl]-7β-amino-ceph-3-em-4-carboxylate as a brown oil; nmr (CDCl₃) 3.51m, 2H (2-CH₂); 3.85s, 3H (N-Me); ~3.9, 2H (3'-CH₂, overlapping by N-Me); 3.75d, 3.95d, J 51, 2H (H-6 + H-7); 6.1dt, J 16, 7.5 Hz, 1H (H-2'); 6.88d, J 16 Hz, 1H (H-1'); 7.04s, 1H (CHφ₂); 7.1–7.6m, 10H (φ₂).

Similarly, benzhydryl 3-[3-(1,2,4-triazol-5-ylthio)-prop-1-(t)-enyl]-7β-aminoceph-3-em-4-carboxylate is prepared by following the same procedure using benzhydryl 3-[3-(1,2,4-triazol-5-ylthio)-prop-1-(t)-enyl]-7β-(thiophen-2-yl-acetamido)-ceph-3-em-4-carboxylate as the starting material.

EXAMPLE 4A

This example illustrates step 4A of the process of the invention. In this example, 0.2 g. of benzhydryl 3-[3-(1-methyltetrazol-5-ylthio)-prop-1-(t)-enyl]-7β-(α-thiophen-2-ylacetamido)-ceph-3-em-4-carboxylate ester (0.2 g.) and anisole (0.5 ml.) are stirred together at 0°C and 2.5 ml. of trifluoroacetic acid added. The mixture is stirred vigorously for two minutes and then rapidly evaporated to dryness under reduced pressure. The resulting crude 3-[3-(1-methyltetrazol-5-ylthio)-prop-1-(t)-enyl]-7β-(α-thiophen-2-ylacetamido)-ceph-3-em-4-carboxylic acid is dissolved in tetrahydrofuran and then filtered. The resulting filtrate is treated with an excess of a solution of sodium 2-ethylhexanoate in tetrahydrofuran and then evaporated to dryness. The residue is mixed with isopropanol and stirred at room temperature for one hour. The resulting solid is collected by filtration, washed three times with isopropanol and dried under vacuum affording 0.11 g. of sodium 3-[3-(1-methyltetrazol-5-ylthio)-prop-1-(t)-enyl]-7β-(α-thiophen-2-ylacetamido)-ceph3-em-4-carboxylate as an off-white powder, which decomposes before melting; uv (water) 296 nm (ε20,100); ir (KBr) 1760, 1660, 1600 cm⁻¹; nmr (DMSO-d₆) 3.4 bs, 2H (2-CH₂); 3.75s 2H

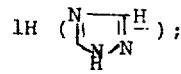

3.92s, 3H (N-Me); 4.00d, J 7.5 Hz, 2H (3'-CH₂); 4.97d, J 5 Hz, 1H (6-H); 5.47dd, J 5, 9 Hz, 1H (7-H); 5.71dt, J 7.5, 15 Hz, 1H (2'-H); 6.8-7.0m, 2H (thiophene); 7.10d, J 15 Hz, 1H (1'-H); 7.25-7.4m, 1H (thiophene); 9.06d, J 9 Hz, 1H (NH).

The sodium salt of 7β-(α-thiophen-2-ylacetamido)-3-[3-(1,2,4-triazol-5-ylthio)-prop-1-(t)-enyl]-ceph-3-em-4-carboxylic acid is prepared by stirring a mixture containing 80 mg. of benzhydryl 3-[3-(1-methyltetrazol-5-ylthio)-prop-1-(t)-enyl[-7β-(α-thiophen-2-ylacetamido)-ceph-3-em-4-carboxylate and 0.5 ml. anisole at 0°C and then adding 2.5 ml. of trifluoroacetic acid. The mixture is stirred vigorously for two minutes, then rapidly evaporated to dryness under reduced pressure. The resulting crude 7β-(α-thiophen-2-ylacetamido)-3-[3-(1,2,4-triazol-5-ylthio)-prop-1(t)-enyl]-ceph-3-em-4-carboxylic acid is mixed with ethyl ether, yielding a white solid which separates and is then collected by filtration. The solid is dissolved in tetrahydrofuran, filtered, and the filtrate treated with an excess of a solution of sodium 2-ethylhexanoate in tetrahydrofuran. The mixture is evaporated to dryness and the residue mixed with isopropanol. A white solid separates and is then collected by filtration, washed several times with isopropanol and dried under vacuum affording 42 mg. of sodium 7β-(α-thiophen-2-ylacetamido)-3-[3-(1,2,4-triazol-5-ylthio)-prop-1-(t)-enyl]-ceph-3-em-4-carboxylate; which also decomposes before melting; uv (water) 297 nm (ε19,000); ir (KBr) 1755, 1660, 1610 cm⁻¹; nmr (DMSO-d₆): 3.44s, 2H (2-CH₂); 3.78s,

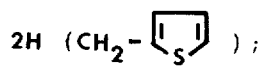

3.8bd, 2H (3'-CH₂); 4.98d, J 5 Hz, 1H (6-H); 4.49dd, J 5, 9 Hz, 1H (7-H); 5.74dt, J 7, 15 Hz, 1H (2'-H); 6.8-7.0m. 2H (thiophene); 7.07d, J 15 Hz, 1H (1'-H); 7.3-7.5m, 1H (thiophene); 8.22s, 1H (N⎯NH / N⎯N H);

9.08d, J 9 Hz, 1H (NHCO).

EXAMPLE 5

This example illustrates the acrylation steps of the process for preparing the compounds of the invention. In this example, a mixture of 0.15 g. of diphenylmethyl 7β-amino-3-[3-(1-methyltetrazol-5-ylthio)-prop-1-(t)-enyl]-ceph-3-em-4-carboxylate and 0.5 ml. of pyridine, in 5 ml. of chloroform is stirred at room temperature and 0.1 g. of 1H-tetrazol-1-ylacetyl chloride, in 2 ml. of chloroform, is added. The mixture is stirred for 30 minutes, then diluted further with chloroform, washed with dilute aqueous hydrochloric acid and brine, dried over anhydrous sodium sulfate, and then evaporated under reduced pressure yielding 0.25 g. of a brown oily residue. The residue is purified using thick layer chromatography on silica gel eluting with acetone/dichloromethane, 1:4, affording 0.12 g. of diphenylmethyl 7β-[α-(1H)-tetrazol-1-ylacetamido]-3-[3-(1-methyltetrazol-5-ylthio)-prop-1-(t)-enyl]-ceph-3-em-4-carboxylate as a white glass; nmr (CDCl₃): 3.45bs, 2H (2-CH$_2$); 3.78s, 3H (N-Me); 3.9bd, J 7 Hz, 2H, (3'-CH$_2$); 4.92d, J 5 Hz, 1H (6-H); 5.19s, 2H (>N—CH$_2$CO); 5.77dd, J 5, 9 Hz, 1H (7-H); 6.12dt, J 7, 16 Hz, 1H (2'-H); 6.8-7.6m, (CH$\phi_2$+1-H); 8.89s,

Similarly, diphenylmethyl 7β-[α-(1H)-tetrazol-1-yl-acetamido]-3-[3-(1,2,4-triazol-5-ylthio)-prop-1-(t)-enyl]ceph-3-em-4-carboxylate is prepared by following the same procedure but using diphenylmethyl 7β-amino-3-[3-(1-methyltetrazol-5-ylthio)-prop-1-(t)-enyl]-ceph-3-em-4-carboxylate.

EXAMPLE 6

This example illustrates hydrolysis of the carboxylate ester protecting group and preparation of the salts of the invention.

In this example, a mixture of 0.11 g. of diphenyl-methyl 7β-(α-(1H)-tetrazol-1-ylacetamido)-3-[3-(1-methyltetrazol-5-ylthio)-prop-1-(t)-enyl]-ceph-3-em-4-carboxylate and 0.5 ml. of anisole is stirred at 0°C and 2.5 ml. of trifluoroacetic acid is then added. The mixture is stirred vigorously for two minutes, then rapidly evaporated to dryness under reduced pressure. The resulting crude 7β-(α-(1H)-tetrazol-1-ylacetamido)-3-[3-(1-methyltetrazol-5-ylthio)-prop-1-(t)-enyl]-ceph-3-em-4-carboxylic acid is treated with ethyl ether.

A white solid separates and is collected by filtration and then dissolved in tetrahydrofuran and filtered, and the filtrate treated with an excess of a solution of sodium 2-ethylhexanoate in tetrahydrofuran. The mixture is evaporated to dryness and the resulting residue mixed with isopropanol. A white solid separates and is collected by filtration, washed three times with isopropanol and dried under vacuum to give 4.5 mg. of sodium 7β-(α-(1H)-tetrazol-1-ylacetamido)-3-[3-(1-methyltetrazol-5-ylthio)-prop-1-(t)-enyl]-ceph-3-em-4-carboxylate as a white powder, which decomposes without melting above 170°C; uv (water) 296 nm (ε21,000); ir (KBr) 1775, 1700, 1615 cm$^{-1}$; nmr (DMSO-d$_6$): 3.44s, 2H (2-CH$_2$); 3.92s, 3H (N-Me); 3.99d, J 7 Hz, 2H (3'-CH$_2$); 4.99d, J 5 Hz, 1H (6-H); 5.37s, 2H (>N—CH$_2$CO); 5.51dd, J 5, 9 Hz, 1H (7-H); 5.73dt, J 7, 16 Hz, 1H (2'-H); 7.11d, J 16 Hz, 1H (1'-H); 9.37s,

9.5d, J 9 Hz, 1H (NH).

Similarly, sodium 7β-(α-(1H)-tetrazol-1-ylacetamido)-3-[3-(1,2,4-triazol-5-ylthio)-prop-1-(t)-enyl]-ceph-3-em-4-carboxylate is prepared by following the same procedure but using diphenylmethyl 7β-(α-(1H)-tetrazol-1-ylacetamido)-3-[3-(1,2,4-triazol-5-ylthio)-prop-1-(t)-enyl]-ceph-3-em-4-carboxylate.

EXAMPLE 7

This example illustrates the acylation steps for preparing the compounds of the invention. In this example, a mixture of 0.15 g. of diphenylmethyl 7β-amino-3-[3-(1-methyltetrazol-5-ylthio)-prop-1-(t)-enyl]-ceph-3-em-4-carboxylate and 0.5 ml. of pyridine, in 5 ml. of chloroform, is stirred at 0°C and then 0.1 ml. of phenoxyacetyl chloride is added, and the mixture stirred for 30 minutes. The mixture is then diluted with ethyl acetate and washed successively with dilute aqueous hydrochloric acid, dilute aqueous sodium bicarbonate solution and brine. The mixture is dried over anhydrous sodium sulfate, and then evaporated to dryness, under reduced pressure, giving 0.25 g. of a brown oil. The oil is purified via thick-layer chromatography on silica gel eluting with acetone/dichloromethane, 1:20, affording 0.12 g. of the diphenyl 3-[3-(1-methyltetrazol-5-ylthio)-prop-1-(t)-enyl]-7β-phenoxyacetamido-ceph-3-em-4-carboxylate is obtained as a pale yellow oil; nmr (CDCl$_3$) 3.49s, 2H (2-CH$_2$); 3.38s, 3H (N-Me); 3.19d, J 7 Hz, 2H (3'-CH$_2$); 4.56s, 2H (OCH$_2$CO); 5.03d, J 5 Hz, 1H (6-H); 5.94dd, J 5, 9 Hz, 1H (7-H); 6.13dt, J 7, 16 Hz, 1H (2'-H); 6.8-7.6m (CH$\phi_2$+$\phi$o+1'H+NH).

Similarly, diphenylmethyl 7β-phenoxyacetamido-3-[3-(1,2,4-triazol-5-ylthio)-prop-1-(t)-enyl]-ceph-3-em-4-carboxylate is prepared by following the same procedure but using diphenylmethyl 7β-amino-3-[3-(1-methyltetrazol-5-yl-thio)-prop-1-(t)-enyl]-ceph-3-em-4-carboxylate.

EXAMPLE 8

This example illustrates hydrolysis of the carboxylate ester protecting group and the preparation of the salts of the invention. In this example, a mixture of 80 mg. of diphenylmethyl 3-[3-(1-methyltetrazol-5-ylthio)-prop-1-(t)-enyl]-7β-(α-phenoxyacetamido)-ceph-3-em-4-carboxylate and 0.5 ml. of anisole is stirred at 0°C and 2.5 ml. of trifluoroacetic acid is then added. The mixture is stirred vigorously for two minutes, then rapidly evaporated to dryness under reduced pressure. The resulting crude 3-[3-(1-methyltetrazol-5-ylthio)-prop-1-(t)-enyl]-7β-(α-phenoxyacetamido)-ceph-3-em-4-carboxylic acid residue is treated with ethyl ether, and affording a pale yellow solid which is then collected by filtration. The solid is dissolved in tetrahydrofuran, filtered, and the filtrate treated with an excess of a solution of sodium 2-ethylhexanoate in tetrahydrofuran. The mixture is evaporated to dryness. Isopropanol is added to the residue yielding a white solid, which separates, and is then collected by filtration, washed several times with isopropanol and dried under vacuum to give 35 mg. of sodium 3-[3-(1-methyltetrazol-5-ylthio)-prop-1-(t)-enyl]-7β-(α-phenoxyacetamido)-ceph-3-em-4-carboxylate; decomposes without melting; uv (water) 293 nm (ε15,900); ir (KBr) 1765, 1675, 1600 cm$^{-1}$; nmr (DMSO-d$_6$): 3.4bs, 2H (2-CH$_2$); 3.92s, 3H (N-Me); 3.99d, J 7 Hz, 2H (3'-CH$_2$); 4.60s, 2H (OCH$_2$CO); 5.00d, J 5 Hz, 1H (6-H); 5.50dd, J 5, 9 Hz, 1H (7-H); 5.72dt, J 7, 15 Hz, 1H (2'-H); 6.8-7.4m, 6H ($\phi$+1'-H); 9.00d, J 9 Hz, 1H (NH).

Similarly, sodium 7β-(α-phenoxyacetamido)-3-[3-(1,2,4-triazol-5-ylthio)-prop-1-(t)-enyl]-ceph-3-em-4-carboxylate is prepared by following the same procedure but using diphenylmethyl 7β-(α-phenoxyacetamido)-3-[3-(1,2,4-triazol5-ylthio)-prop-1-(t)-enyl]-ceph-3-em-4-carboxylate.

EXAMPLE 9

This example illustrates the acylation steps for preparing the compounds of the invention. In this example, a mixture of 0.15 g. of diphenylmethyl 7β-amino-3-

[3-(1-methyltetrazol-5-ylthio)-prop-1-(t)-enyl]-ceph-3-em-4-carboxylate and 0.5 ml. of pyridine, in 5 ml. of chloroform, is stirred at 0°C and then 0.1 ml. of phenylthioacetyl chloride is added, and the mixture stirred for 30 minutes. The mixture is then diluted with ethyl acetate and washed successively with dilute aqueous hydrochloric acid, dilute aqueous sodium bicarbonate solution and brine. The mixture is dried over anhydrous sodium sulfate, evaporated to dryness, under reduced pressure. The residue is purified via thick-layer chromatography on silica gel eluting with acetone/dichloromethane, 1:20, affording diphenyl 3-[3-(1-methyltetrazol-5-ylthio)-prop-1-(t)-enyl]-7β-phenylthioacetamido-ceph-3-em-4-carboxylate.

Similarly, diphenylmethyl 7β-phenylthioacetamido-3-[3-(1,2,4-triazol-5-ylthio)-prop-1-(t)-enyl]-ceph-3-em-4-carboxylate is prepared by following the same procedure but using diphenylmethyl 7β-amino-3-[3-(1-methyltetrazol-5-ylthio)-prop-1-(t)-enyl]-ceph-3-em-4-carboxylate.

EXAMPLE 10

This example illustrates hydrolysis of the carboxylate ester protecting group and the preparation of the salts of the invention. In this example a mixture of 80 mg. of diphenylmethyl 3-[3-(1-methyltetrazol-5-ylthio)-prop-1-(t)-enyl]-7β-(α-phenylthioacetamido)-ceph-3-em-4-carboxylate and 0.5 ml. of anisole is stirred at 0°C and 2.5 ml. of trifluoroacetic acid is then added. The mixture is stirred vigorously for two minutes, then rapidly evaporated to dryness under reduced pressure. The crude 3-[3-(1-methyltetrazol-5-ylthio)-prop-1(t)-enyl]7β-(α-phenylthioacetamido)-ceph-3-em-4-carboxylic acid residue is treated with ethyl ether, and then filtered. The collected solid is dissolved in tetrahydrofuran, filtered, and the filtrate treated with an excess of a solution of sodium 2-ethylhexanoate in tetrahydrofuran. The mixture is evaporated to dryness. The residue is mixed with isopropanol and then filtered. The collected solid is washed several times with isopropanol and then dried under vacuum affording sodium 3-[3-(1-methyltetrazol-5-ylthio)-prop-1-(t)-enyl]-7β-(α-phenylthioacetamido)-ceph-3-em-4-carboxylate.

Similarly, sodium 7β-(α-phenylthioacetamido)-3-[3-(1,2,4-triazol-5-ylthio)-prop-1-(t)-enyl]-ceph-3-em-4-carboxylate is prepared by following the same procedure using diphenylmethyl 7β-(α-phenylthioacetamido)-3-[3-(1,2,4-triazol-5-ylthio)-prop-1-(t)-enyl[ceph-3-em-4-carboxylate.

EXAMPLE 11

This example illustrates the acylation steps of the process for preparing the compounds of the invention.

In this example, a solution of 0.25 g. of diphenylmethyl 7β-amino-3-[3-(1-methyltetrazol-5-ylthio)-prop-1-(t)-enyl]-ceph-3-em-4-carboxylate in 10 ml. chloroform is treated with 0.15 g. of trifluoromethylthioacetic acid and 0.2 g. of dicyclohexylcarbodiimide. The mixture is stirred at room temperature for two hours and then filtered to remove dicyclohexylurea. The filtrate is evaporated to dryness and the residue purified using thick-layer chromatography on silica gel eluting with acetone/dichloromethane, 1:20, affording diphenylmethyl 3-[3-(1-methyltetrazol-5-ylthio)-prop-1-(t)-enyl]-7β-(α-trifluoromethylthioacetamido)-ceph-3-em-4-carboxylate.

Similarly, diphenylmethyl 3-[3-(1,2,4-triazol-5-ylthio)-prop-1-(t)-enyl]-7β-(α-trifluoromethylthioacetamido)-ceph-3-em-4-carboxylate is prepared via the some procedure but using 7β-amino-3-[3-(1-methyltetrazol-5-ylthio)-prop-1-(t)-enyl]-ceph-3-em-4-carboxylate.

EXAMPLE 12

This example illustrates hydrolysis of the carboxylate ester protecting group and the preparation of the salts of the invention. In this example, a mixture of 80 mg. of diphenylmethyl 3-[3-(1-methyltetrazol-5-ylthio)-prop-1-(t)-enyl]-7β-(α-trifluoromethylthioacetamido)-ceph-3-em-4-carboxylate and 0.5 ml. of anisole is stirred at 0°C and 2.5 ml. of trifluoroacetic acid is then added. The mixture is stirred vigorously for two minutes, then rapidly evaporated to dryness under reduced pressure. The crude 3-[3-(1-methyltetrazol-5-ylthio)-prop-1-(t)-enyl]-7β-(α-trifluoromethylthioacetamido)-ceph-3-em-4-carboxylic acid residue is treated with ethyl ether, and the filtered. The collected solid is dissolved in tetrahydrofuran, filtered, and the filtrate treated with an excess of a solution of sodium 2-ethylhexanoate in tetrahydrofuran. The mixture is evaporated to dryness. The residue is mixed with isopropanol and then filtered. The collected solid is washed several times with isopropanol and dried under vacuum affording sodium 3-[3-(1-methyltetrazol-5-ylthio)-prop-1-(t)-enyl]-7β-(α-trifluoromethylthioacetamido)-ceph-3-em-4-carboxylate.

Similarly, sodium 3-[3-(1,2,4-triazol-5-ylthio)-prop-1-(t)-enyl]-7β-(α-trifluoromethylthioacetamido)-ceph-3-em-4-carboxylate is prepared by following the same procedure but using diphenylmethyl 3-[3-(1,2,4-triazol-5-ylthio)-prop-1-(t)-enyl]-7β-(α-trifluoromethylthioacetamido)-ceph-3-em-4-carboxylate.

EXAMPLE 13

This example illustrates the acylation steps of the process for preparing the compounds of the invention.

In this example, a solution of 0.25 g. of diphenyl 7β-amino-3-[3-(1-methyltetrazol-5-ylthio)-prop-1-(t)-enyl]-ceph-3-em-4-carboxylate and 0.2 g. of sydnon-3-acetic acid in ethyl acetate is treated with 0.20 g. of dicyclohexyl carbodiimide. The mixture is stirred for two hours at room temperature, then filtered and evaporated to dryness. The residue is subjected to thick-layer chromatography on silica gel eluting with acetone/dichloromethane, 1:10, affording diphenylmethyl 3-[3-(1-methyltetrazol-5-ylthio)-prop-1-(t)-enyl]-7β-(sydnon-3-ylacetamido)-ceph-3-em-4-carboxylate.

Similarly, diphenylmethyl 7β-(sydnon-3-ylacetamido)-3-[3-(1,2,4-triazol-5-ylthio)-prop-1-(t)-enyl]-ceph-3-em-4-carboxylate is prepared by following the same procedure but using diphenylmethyl 7β-amino-3-[3-(1-methyltetrazol-5-yl-thio)-prop-1-(t)-enyl]-ceph-3-em-4-carboxylate.

EXAMPLE 14

This example illustrates hydrolysis of the carboxylate ester protecting group and the preparation of the salts of the invention. In this example, a mixture of 80 mg. of diphenylmethyl 3-[3-(1-methyltetrazol-5-ylthio)-prop-1-(t)-enyl]-7β-(α-sydnon-3-ylacetamido)-ceph-3-em-4-carboxylate and 0.5 ml. of anisole is stirred at 0°C and 2.5 ml. of trifluoroacetic acid is then added. The mixture is stirred vigorously for two minutes, then rapidly evaporated to dryness under reduced pressure. The crude 3-[3-(1-methyltetrazol-5-ylthio)-prop-1-(t)-enyl]-7β-(α-sydnon-3-ylacetamido)-ceph- 3-em-4-carboxylic acid residue is treated with ethyl ether, and then filtered. The collected solid is dissolved in tetrahydrofuran, filtered, and the filtrate treated with an excess of a solution of sodium 2-ethylhexanoate in tetrahydrofuran. The mixture is evaporated to dryness. The residue is mixed with isopropanol and then filtered. The collected solid is washed several times with isopropanol and then dried under vacuum affording sodium 3-[3-(1-methyltetrazol-5-ylthio)-prop-1-(t)-enyl]-7-(α-sydnon-3-ylacetamido)-ceph-3-em-4-carboxylate.

Similarly, sodium 7-(α-sydnon-3-ylacetamido)-3-[3-(1,2,4-triazol-5-ylthio)-prop-1-(t)-enyl]-ceph-3-em-4-carboxylate is prepared by following the same procedure but using diphenylmethyl 7-(α-sydnon-3-ylacetamido)-3-[3-(1,2,4-triazol-5-ylthio)-prop-1-(t)-enyl]-ceph-3-em-4-carboxylate.

EXAMPLE 15

For purposes of purifying and isolating the free acids, a small portion (10 mg.) of each of the sodium salt products, prepared according to Examples 4A, 6, 8, 10, 12, and 14, is respectively converted back to the 4-carboxylic acid by dissolving in water, adjusting the pH to 1.5 using dilute hydrochloric acid and extracting twice with ethyl acetate. The combined extracts are washed with brine, dried and evaporated to dryness. The residue is mixed with ethyl ether and the purified 4-carboxylic acid product collected by filtration.

Obviously many modifications and variations of the of the invention, described hereinabove and below and in the claims, can be made without departing from the essence and scope thereof.

What is claimed is:
1. A compound selected from the group having the formula:

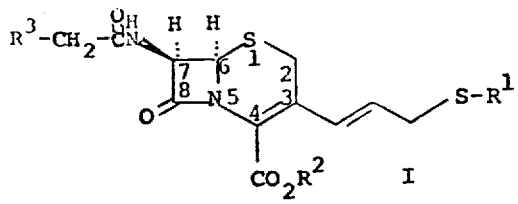

wherein
the propenyl double bond is trans;
$R^1$ is 1-methyltetrazol-5-yl; or 1,2,4-triazol-5-yl;
$R^2$ is hydrogen, diphenylmethyl, p-methoxybenzyl, p-nitrobenzyl, o-nitrobenzyl, benzyl, t-butyl, 2,2,2-trichloroethyl, phenacyl or pivaloyloxymethyl;
$R^3$ is thiophen-2-yl; trifluormethylthio, phenoxy, phenylthio, (1H)-tetrazol-1-yl or sydnon-3-yl;
and pharmaceutically acceptable salts thereof.

2. The compound of claim 1 wherein said compound is selected from the group having the formula:

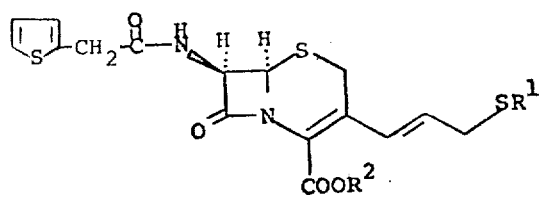

wherein
$R^1$ and $R^2$ are as defined in claim 1,
and pharmaceutically acceptable salts thereof.

3. The compound of claim 2 wherein $R^2$ is diphenylmethyl.

4. The compound of claim 2 wherein $R^2$ is hydrogen and pharmaceutically acceptable salts thereof.

5. The compound of claim 2 wherein $R^1$ is 1-methyltetrazol-5-yl.

6. The compound of claim 5 wherein said compound is selected from the group of 3-[3-(1-methyltetrazol-5-ylthio)-prop-1-(t)-enyl]-7β-(α-thiophen-2-ylacetamido)-ceph-3-em-4-carboxylic acid and pharmaceutically acceptable salts thereof.

7. The compound of claim 6 wherein said compound is a sodium salt.

8. The compound of claim 9 wherein $R^1$ is 1,2,4-triazol-5-yl.

9. The compound of claim 8 wherein said compound is selected from the group of 7β-(α-thiophen-2-ylacetamido)-3-[3-(1,2,4-triazol-5-ylthio)-prop-1-(t)-enyl]-ceph-3-em-4-carboxylic acid and pharmaceutically acceptable salts thereof.

10. The compound of claim 9 wherein said compound is a sodium salt.

11. The compound of claim 1 wherein said compound is selected from the group having the formula:

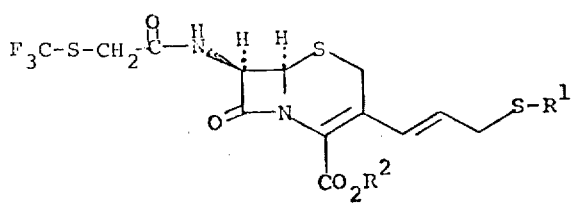

wherein
$R^1$ and $R^2$ are as defined in claim 1,
and pharmaceutically acceptable salts thereof.

12. The compound of claim 11 wherein $R^2$ is diphenylmethyl.

13. The compound of claim 11 wherein $R^2$ is hydrogen and pharmaceutically acceptable salts thereof.

14. The compound of claim 11 wherein $R^1$ is 1-methyltetrazol-5-yl.

15. The compound of claim 14 wherein said compound is selected from the group of 3-[3-(1-methyltetrazol-5-ylthio)-prop-1-(t)-enyl]-7β-(α-trifluoromethylthioacetamido)-ceph-3-em-4-carboxylic acid and pharmaceutically acceptable salts thereof.

16. The compound of claim 15 wherein said compound is a sodium salt.

17. The compound of claim 11 wherein $R^1$ is 1,2,4-triazol-5-yl.

18. The compound of claim 17 wherein said compound is selected from the group of 3-[3-(1-methyltetrazol-5-ylthio)-prop-1-(t)-enyl]-7β-(α-trifluoromethylthioacetamido)-ceph-3-em-4-carboxylic acid and pharmaceutically acceptable salts thereof.

19. The compound of claim 18 wherein said compound is a sodium salt.

20. The compound of claim 1 wherein said compound is selected from the group having the formula

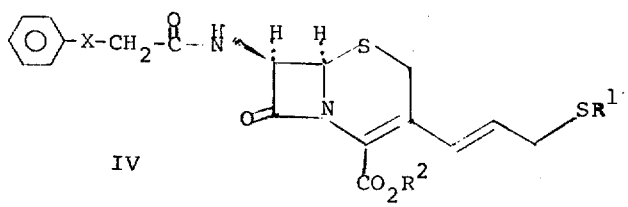

IV wherein
X is oxo or thio and
R¹ and R² are as defined in claim 1,
and pharmaceutically acceptable salts thereof.

21. The compound of claim 20 wherein R² is diphenylmethyl.

22. The compound of claim 20 wherein R² is hydrogen and pharmaceutically acceptable salts thereof.

23. The compound of claim 20 wherein R¹ is 1-methyltetrazol-5-yl.

24. The compound of claim 23 wherein said compound is selected from the group of 3-[3-(1-methyltetrazol-5-ylthio)-prop-1-(t)-enyl]-7β-(α-phenyoxyacetamido)-ceph-3-em-4-carboxylic acid and pharmaceutically acceptable salts thereof.

25. The compound of claim 24 wherein said compound is a sodium salt.

26. The compound of claim 23 wherein said compound is selected from the group of 3-[3-(1-methyltetrazol-5-ylthio)-prop-1-(t)-enyl]-7β-(α-phenylthioacetamido)-ceph-3-em-4-carboxylic acid and pharmaceutically accepted salts thereof.

27. The compound of claim 26 wherein said compound is a sodium salt.

28. The compound of claim 20 wherein R¹ is 1,2,4-triazol-5-yl.

29. The compound of claim 28 wherein said compound is selected from the group of 7β-(α-phenoxyacetamido)-3-[3-(1,2,4-triazol-5-ylthio)-prop-1-(t)-enyl]-ceph-3-em-4-carboxylic acid and pharmaceutically acceptable salts thereof.

30. The compound of claim 29 wherein said compound is a sodium salt.

31. The compound of claim 28 wherein said compound is selected from the group of 7β-(α-phenylthioacetamido)-3-[3-(1,2,4-triazol-5-ylthio)-prop-1-(t)-enyl]-ceph-3-em-4-carboxylic acid and pharmaceutically acceptable salts thereof.

32. The compound of claim 31 wherein said compound is a sodium salt.

33. The compound of claim 1 wherein said compound is selected from the group having the formula:

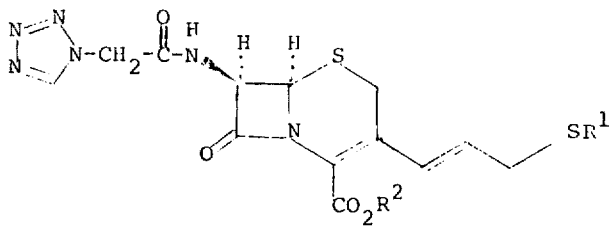

IV wherein
R¹ and R² are as defined in claim 1,
and pharmaceutically acceptable salts thereof.

34. The compound of claim 33 wherein R² is diphenylmethyl.

35. The compound of claim 33 wherein R² is hydrogen and pharmaceutically acceptable salts thereof.

36. The compound of claim 33 wherein R¹ is 1-methyltetrazol-5-yl.

37. The compound of claim 36 wherein said compound is selected from the group of 7β-[α-(1H)-tetrazol-1-ylacetamido]-3-[3-(1-methyltetrazol-5-ylthio)-prop-1-(t)-enyl]-ceph-3-em-4-carboxylic acid and pharmaceutically acceptable salts thereof.

38. The compound of claim 37 wherein said compound is a sodium salt.

39. The compound of claim 33 wherein R¹ is 1,2,4-triazol-5-yl.

40. The compound of claim 39 wherein said compound is selected from the group of 7β-[α-(1H)-tetrazol-1-ylacetamido]-3-[3-(1,2,4-triazol-5-ylthio)-prop-1-(t)-enyl]-ceph-3-em-4-carboxylic acid and pharmaceutically acceptable salts thereof.

41. The compound of claim 1 wherein said compound is selected from the group having the formula:

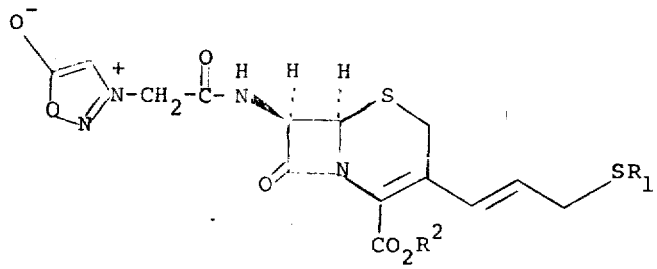

V wherein
R$^1$ and R$^2$ are as defined in claim 1,
and pharmaceutically acceptable salts thereof.

42. The compound of claim 41 wherein R$^2$ is diphenylmethyl.

43. The compound of claim 41 wherein R$^2$ is hydrogen and pharmaceutically acceptable salts thereof.

44. The compound of claim 41 wherein R$^1$ is 1-methyltetrazol-5-yl.

45. The compound of claim 44 wherein said compound is selected from the group of 7β-[α-sydnon-3-ylacetamido]-3-[3-(1-methyltetrazol-5-ylthio)-prop-1-(t)-enyl]-ceph-3-em-4-carboxylic acid and pharmaceutically acceptable salts thereof.

46. The compound of claim 45 wherein said compound is a sodium salt.

47. The compound of claim 41 wherein R$^1$ is 1,2,4-triazol-5-yl.

48. The compound of claim 47 wherein said compound is selected from the group of 7β-[α-sydnon-3-ylacetamido]-3-[3-(1,2,4-triazol-5-ylthio)-prop-1-(t)-enyl]-ceph-3-em-4-carboxylic acid and pharmaceutically acceptable salts thereof.

49. The compound of claim 1 wherein said compound is selected from the group of

7β-(α-(1H)-tetrazol-1-ylacetamido)-3-[3-(1-methyltetrazol-5-ylthio)-prop-1-(t)-enyl]-ceph-3-em-4-carboxylic acid;

7β-(α-trifluoromethylthioacetamido)-3-[3-(1-methyltetrazol-5-ylthio)-prop-1-(t)-enyl]-ceph-3-em-4-carboxylic acid;

7β-(α-sydnon-3-ylacetamido)-3-[3-(1-methyltetrazol-5-ylthio)-prop-1-(t)-enyl]-ceph-3-em-4-carboxylic acid; and pharmaceutically acceptable salts thereof.

50. A process for preparing the compounds of claim 2 which comprises rearranging the C-2(3) position double bond of the corresponding 3-[3-heterocycleylthio)-prop-1-(t)-enyl]-7β-(thiophen-2-yl-acetamido)-ceph-2-em-4-carboxylate to C6 C-3(4) position to yield the corresponding R$^2$ ester of claim 2 and optionally cleaving the ester group to yield the corresponding free acid and optionally treating the acid with a pharmaceutically acceptable cation to yield the corresponding salt.

51. A process for preparing the compounds of claim 1 which comprises acylating the corresponding 7β-amino-cepheme 4-carboxylic acid or carboxylic ester with an acylating reagent corresponding to the desired R$^3$ acetamido substituent and optionally hydrolyzing said carboxylic ester and if desired treating the 4-carboxylic acid product with a pharmaceutically acceptable cation to yield the corresponding salt.

52. An antibacterial composition comprising an antibiotic agent selected from the compounds of claim 1 wherein R$^2$ is H, and pharmaceutically acceptable salts thereof, and mixtures of such compounds; and a compatible carrier.

* * * * *